United States Patent [19]
Delany

[11] 3,943,766
[45] Mar. 16, 1976

[54] FLAME IONIZATION DETECTOR STATUS INDICATOR
[75] Inventor: Edward B. Delany, Ridgefield, Conn.
[73] Assignee: The Perkin-Elmer Corporation, Norwalk, Conn.
[22] Filed: Mar. 7, 1975
[21] Appl. No.: 556,295

[52] U.S. Cl. ............... 73/341; 23/254 E; 73/343 R
[51] Int. Cl.² ........................................... G01K 7/02
[58] Field of Search ............ 73/359, 341, 343, 344; 23/254 EF, 254 E; 431/78, 80

[56] References Cited
UNITED STATES PATENTS
2,385,530    9/1945    Paille ..................................... 431/80

Primary Examiner—Donald O. Woodiel
Attorney, Agent, or Firm—S. A. Giarratana; F. L. Masselle; J. M. O'Meara

[57] ABSTRACT

Thermocouples are disposed in the flame exhaust passage and exteriorly on the housing of each ionization detector to monitor the flame status thereof within an environment of widely varying temperature. A temperature differential signal is derived from the thermocouples of each ionization detector, with each temperature differential signal being compared to a common threshold level at which an indication of a flameout condition occurs. The indication of a flameout condition in each ionization detector is varied relative to the temperature differential thereof through a variable gain amplification stage. Switches are disposed for individually interrupting each temperature differential signal and flameout conditions occurring in any one or more of the ionization detectors are identifiable therewith.

11 Claims, 3 Drawing Figures

FLAME IONIZATION DETECTOR STATUS INDICATOR

BACKGROUND OF THE INVENTION

The present invention relates to apparatus by which flameout conditions in ionization detectors are monitored within an environment of widely varying temperature. Flame ionization detectors are commonly used in analytical equipment, such as gas chromatographs, wherein the environmental temperature varies widely and the flame status of each ionization detector must be monitored to assure that the results derived therefrom are accurate. Hitherto, the most common approach taken to the monitoring of flame status in such equipment had been to hold a polished metal object above the flame exhaust and observe whether a fogging condition occurs thereon. Of course, this approach is predicated on the theory that such fogging will only be caused by water vapor in the exhaust when the flame is lighted. Therefore, flame status very often becomes more difficult to detect with this approach when the environmental temperature within the equipment is between room temperature and the temperature of the exhaust.

SUMMARY OF THE INVENTION

It is the object of this invention to provide apparatus for monitoring the flame status of ionization detectors within equipment having an environment between room temperature and the temperature of the flame exhaust.

It is the further object of this invention to provide an adjustable flameout indication set level within such flame status monitoring apparatus.

It is a still further object of this invention to provide flameout indications for a plurality of ionization detectors from a single indicator within such flame status monitoring apparatus.

These objects are accomplished according to the present invention by deriving a flame status signal for each ionization detector through a differential amplifier from thermocouples which are disposed in the flame exhaust passage and on the housing of each ionization detector. The flame status signal from each differential amplifier is directed to a means for indicating a threshold level and the flameout indication thereof is adjustable at each differential amplifier which includes an operational amplifier with a variable negative feedback resistor connected thereto. Switching means for interrupting the flame status signals is disposed between the threshold level indicating means and each differential amplifier with flameout conditions being traced to particular ionization detectors thereby after an indication occurs.

BRIEF DESCRIPTION OF THE DRAWING

The manner in which these and other objects of the present invention are achieved will be best understood by reference to the following description, the appended claims, and the attached drawing, wherein:

DESCRIPTION OF THE PREFERRED EMBODIMENTS

Figure 1:
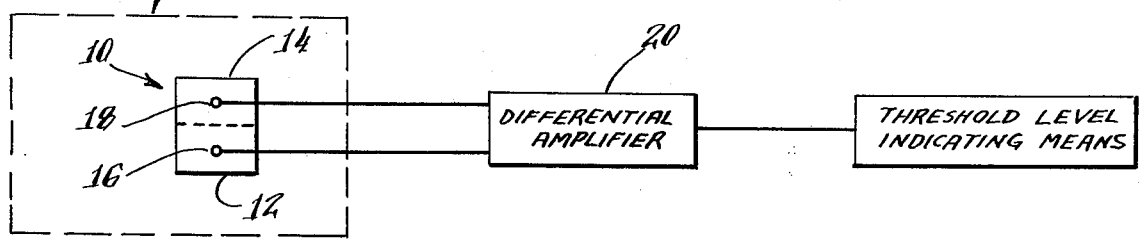
FIG. 1 is a block diagram for the flame monitoring apparatus of this invention.

Turning now to the drawing, and more particularly to FIG. 1, there is illustrated a block diagram for the flame monitoring apparatus of this invention. As is very common in the art of gas chromatography, a flame ionization detector 10 having a housing 12 and a flame exhaust passage 14 is disposed within an environment of widely varying temperature. Thermocouples 16 and 18 are disposed on the housing 12 and in the flame exhaust passage 14, respectively, and each thermocouple output is separately connected to one input of a differential amplifier 20. A means for indicating transgression through a threshold level is connected to the output of the differential amplifier 20.

Of course, a temperature differential will exist between the flame exhaust passage 14 and the housing 12 while the flame of the ionization detector 10 is lighted and when a flameout condition occurs, this temperature differential drops to zero over some period of time. Therefore, by setting the threshold level of the indicating means to correspond with the output from the differential amplifier 20 at some time after the flame extinguishes, a flameout condition will be indicated. Naturally, the response time of a flameout condition indication increases as the threshold level of the indicating means is lowered and environmental temperatures near that of the flame must be considered when the threshold level is set. By locating both thremocouples 16 and 18 on the ionization detector 10, each thermocouple output is affected in substantially the same manner by the environmental temperature and therefore, the flame status is monitored with substantial independence of the environmental temperature encountered. However, those skilled in the art will realize without further explanation that only one of the thermocouples 16 and 18 need be disposed on the ionization detector 10 to develop the temperature differential by which the flame status is monitored with the apparatus of this invention.

Figure 2:
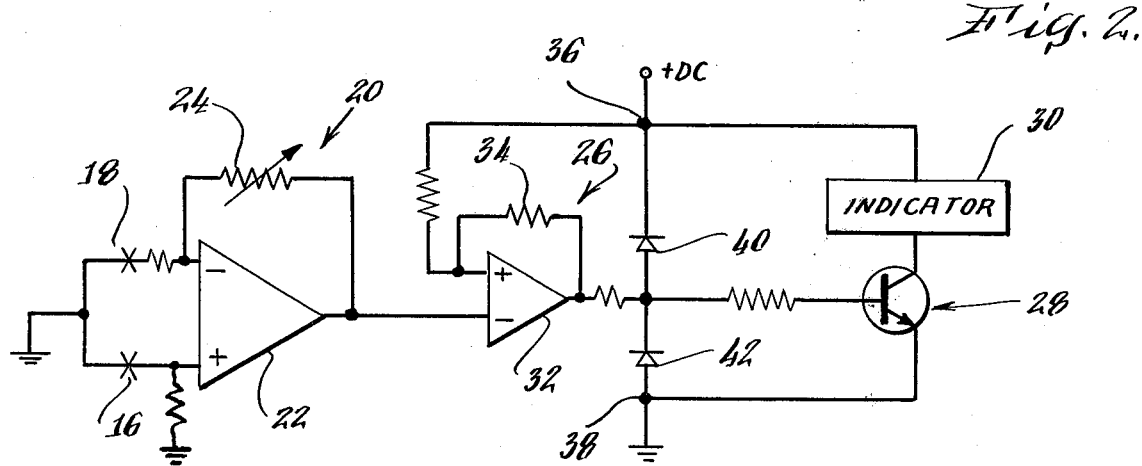
FIG. 2 is a schematic diagram for one embodiment of this invention by which the flame status in a single ionization detector is monitored.

Although many types of differential amplifiers and threshold level indicating means are known in the art, one particularly appropriate circuit for the apparatus of this invention is illustrated in FIG. 2. The differential amplifier 20 in this circuit includes an operational amplifier 22 with a variable negative feedback resistor 24 connected thereto, while the threshold indicating means includes a comparator 26 and a transistor 28 which are interconnected to apply a voltage across an indicator 30 when the output of the differential amplifier 20 transgresses through a threshold level. Any comparator known in the electrical arts could be utilized in the circuit of FIG. 2, however, an operational amplifier 32 having a positive feedback resistor 34 connected thereto is most appropriate. Otherwise, the base of the transistor 28 is connected to the output of the comparator 26 and to each of first and second DC voltage terminals 36 and 38, respectively, through reversebiased diodes 40 and 42, respectively. The inputs of the comparator 26 are connected separately to the first DC voltage terminal 36 and to the output of the differential amplifier 20. Also, the first DC voltage terminal 36 is connected to the collector of the transistor 28 through the indicator 30, while the second DC voltage terminal 28 is connected to the emitter of the transistor 28. Although the transistor 28 is illustrated as an NPN type in FIG. 2, those skilled in the art will certainly recognize that a PNP type could have been utilized therein. Furthermore, such artisans will also recognize that the input resistors to the operational amplifiers 22 and 32 are conventional in the differential amplifier 20 and the comparator 26 respectively, and the resistors disposed between the output of the comparator 26 and the base of the transistor 28 conventionally relate current to voltage for biasing purposes. Although, the voltages to be applied to the first and second DC voltage terminals 36 and 38 can only be determined after the type of transistor has been selected, a positive DC voltage is applied to the first DC voltage terminal 36 and the second DC voltage terminal 38 is grounded, in the circuit of FIG. 2.

Because the comparator 26 in the circuit of FIG. 2 has an inverted output relative to its predominant input, the transistor 28 is non-conductive until the output from the differential amplifier 20 transgresses the positive level on the first DC voltage terminal 36. Therefore, that positive level is the threshold at which the transistor 28 becomes conductive to apply a voltage across the indicator 30 from between the first and second DC voltage terminals 36 and 38. Of course, the output from the differential amplifier 20 corresponds to the temperature differential by which the flame status is monitored and this output can be set to the threshold level for any magnitude of the temperature differential by adjusting the gain of the differential amplifier 20 with the variable negative feedback resistor 24. Otherwise, any negative signal on the base of the transistor 28 is grounded through diode 42, whereas any positive signal thereon is limited to the positive level at the first DC voltage terminal 36 by diode 40. Furthermore, those skilled in the art will certainly recognize that either audio or visual devices could be utilized as the indicator 30 and that only the high and low levels of the voltage which is applied across the indicator 30 would be utilized if the ionization detector were disposed within analytical equipment having readouts adapted for use in digital computation.

Figure 3:
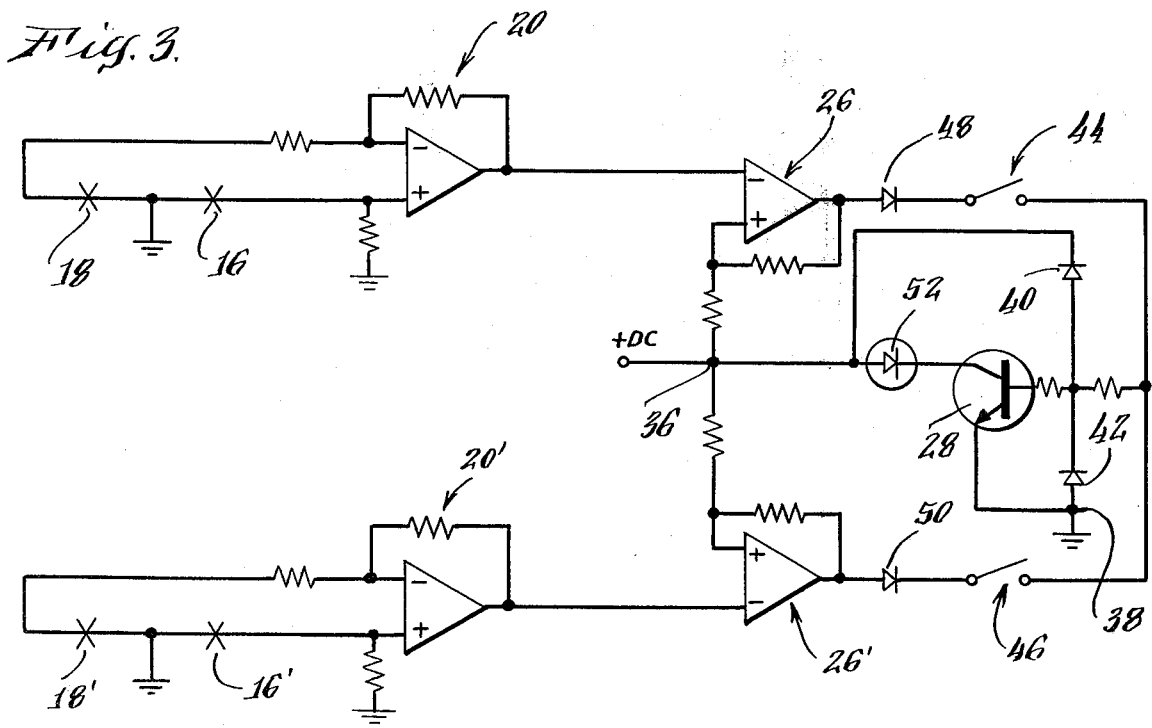
FIG. 3 is a schematic diagram for a second embodiment of this invention by which the flame status in a plurality of ionization detectors is monitored.

The circuit of FIG. 2 can be readily modified to individually monitor the flame status in a plurality of ionization detectors, as illustrated in FIG. 3. Thermocouples 16' and 18' respectively, are disposed on a housing and in a flame exhaust passage of a second ionization detector in the circuitry of FIG. 3. The outputs of thermocouples 16' and 18' are separately connected to the inputs of a second differential amplifier 20'. A second comparator 26' is disposed with the inputs thereof connected separately to the first DC voltage terminal 36 and to the output of the second differential amplifier 20'. The output of the second comparator 26' is commonly connected with the output of the first comparator 26 to the base of the transistor 28. Switching means is disposed between the base of the transistor 28 and the output from each of the comparators 26 and 26' for independently interrupting current flow therebetween, such as single pole, single throw switches 44 and 46. Diodes 48 and 50, respectively, are also disposed between the base of the transistor 28 and the output from each of the comparators 26 and 26' to block passage of any negative signal from the latter. Although any type of indicator could again be utilized in the circuitry of FIG. 3, a light-emitting diode 52 is disposed therein such that a voltage is applied thereacross when the transistor 28 is conductive.

Assuming that the switches 44 and 46 are closed, the transistor 28 in the circuitry of FIG. 3 only becomes conductive through the diodes 48 and 50 when the output of either or both comparators 26 and 26' is positive. Of course, this only occurs when the output of either or both differential amplifiers 20 and 20' transgress the threshold level set at the first DC voltage terminal 36, as discussed previously in regard to the circuitry of FIG. 2. Of course, a voltage is applied across the light-emitting diode 52 when the transistor 28 is conductive to provide a visual indication of a flameout condition in either or both of the ionization detectors. Thereafter, the flameout condition is traced to either or both of the ionization detectors by individually opening each of the switches 44 and 46 and then opening both switches 44 and 46 simultaneously until the light-emitting diode 52 is extinguished. Although the flame status of only two ionization detectors is monitored in the circuitry of FIG. 3, those skilled in the art will realize without further explanation that any number of ionization detectors could be monitored with the apparatus of this invention. When the flame status of more than two ionization detectors is monitored with the apparatus of this invention, the switches utilized therein must first be individually opened and thereafter, every possible combination of simultaneously opened switches must be tried until the light-emitting diode 52 is extinguished.

What I claim is:

1. Flame monitoring apparatus for at least one ionization detector within an environment of widely varying temperature, comprising:

a thermocouple disposed in the flame exhaust passage of each ionization detector;

a thermocouple disposed on the housing of each ionization detector;

a differential amplifier for the outputs from said thermocouples of each ionization detector, each said differential amplifier having the inputs thereof separately connected to the thermocouple outputs; and means for indicating when the output from any one of said differential amplifiers transgresses a threshold level.

2. The apparatus of claim 1 wherein each said differential amplifier includes an operational amplifier with a negative feedback resistor connected thereto, said feedback resistors being variable to individually set the differential outputs from said thermocouples to correspond with said threshold level.

3. The apparatus of claim 1 wherein said threshold level indicating means includes an indicator across which a voltage is applied from between first and second voltage terminals by a transistor, said transistor having the base thereof commonly connected to the outputs of said differential amplifiers through a comparator for each such output and separately connected to each said voltage terminal through a reverse-biased diode, each said comparator having the inputs thereof connected separately to said first voltage terminal and to the output of one said differential amplifier, said first voltage terminal also being connected to said indicator and said second voltage terminal also being connected to the emitter of said transistor, said indicator being connected to the collector of said transistor with the voltage being applied thereacross by said transistor after the output from any one of said differential amplifiers reaches the voltage level of said first voltage terminal.

4. The apparatus of claim 3 wherein said indicator includes a light-emitting diode.

5. The apparatus of claim 3 wherein each said comparator includes an operational amplifier.

6. The apparatus of claim 3 wherein said transistor is of the NPN junction type.

7. The apparatus of claim 3 wherein said indicator includes a light-emitting diode and each said comparator includes an operational amplifier.

8. The apparatus of claim 3 wherein said indicator includes a light-emitting diode and said transistor is of the NPN junction type.

9. The apparatus of claim 3 wherein each said comparator includes an operational amplifier and said transistor is of the NPN junction type.

10. The apparatus of claim 3 wherein said indicator includes a light-emitting diode, each said comparator includes an operational amplifier, and said transistor is of the NPN junction type.

11. Flame monitoring apparatus for a pair of ionization detectors within an environment of widely varying temperature, comprising:
   a pair of first thermocouples, said first thermocouples being individually disposed in the flame exhaust passage of one ionization detector;
   a pair of second thermocouples, said second thermocouples being individually disposed on the housing of one ionization detector;
   a pair of differential amplifiers, each said differential amplifier having the inputs thereof connected separately to the outputs from said first and second thermocouples of one ionization detector;
   a pair of comparators, each said comparator having the inputs thereof connected separately to a first voltage terminal and to the output of one said differential amplifier;
   a transistor having the base thereof commonly connected to both outputs from said comparators;
   a pair of diodes, said diodes being individually connected to reverse bias the base of said transistor relative to said first voltage terminal and relative to a second voltage terminal, said second voltage terminal being also connected to the emitter of said transistor;
   switching means disposed between the base of said transistor and each output from said comparators for independently interrupting current flow therebetween; and
   an indicator connected to the collector of said transistor, said first voltage terminal being also connected to said indicator with a voltage from between said first and second voltage terminals being applied across said indicator by said transistor after the output from either of said differential amplifiers reaches the voltage level of said first voltage terminal and thereafter, the flame status of each ionization detector being determinable through said switching means.

* * * * *